United States Patent [19]

Deemer

[11] 4,098,863
[45] Jul. 4, 1978

[54] METHOD FOR MAKING MOUNTING RING FOR DENTAL ARTICULATOR

[76] Inventor: Milton G. Deemer, 148 Best Ave., San Leandro, Calif. 94577

[21] Appl. No.: 760,035

[22] Filed: Jan. 17, 1977

[51] Int. Cl.² .......................... B28B 3/02; B29D 3/00
[52] U.S. Cl. ..................................... 264/275; 264/333
[58] Field of Search .............. 264/259, 271, 275, 299, 264/333; 32/32

[56] References Cited

U.S. PATENT DOCUMENTS

| | | | |
|---|---|---|---|
| 2,941,830 | 6/1960 | Burke | 264/275 |
| 2,979,775 | 4/1961 | White | 264/275 |

*Primary Examiner*—Willard E. Hoag
*Attorney, Agent, or Firm*—Linval B. Castle

[57] ABSTRACT

A method for making a mounting ring for securing dental casts to the base and bow members of an articulator is cast of dental stone or plaster to provide a strong molecular bond as well as the conventional mechanical bond to the plaster dental casts. The mounting ring is readily cast as needed in the dental laboratory using a two-piece mold having a piston with a diameter corresponding to the diameter of the ring and a cylindrical mating resilient base section containing the desired ring pattern and also a vertical post upon which a threaded metal nut may be supported. When appropriately loaded with the nut and the ring material in its liquid state, the base and piston are compressed by hand pressure to form the mounting ring while extruding excess liquid plaster from the space separating the wall of the resilient base and the piston. The threaded metal nut firmly cast in the mounting ring may then be used to secure a dental cast to the articulator.

5 Claims, 2 Drawing Figures

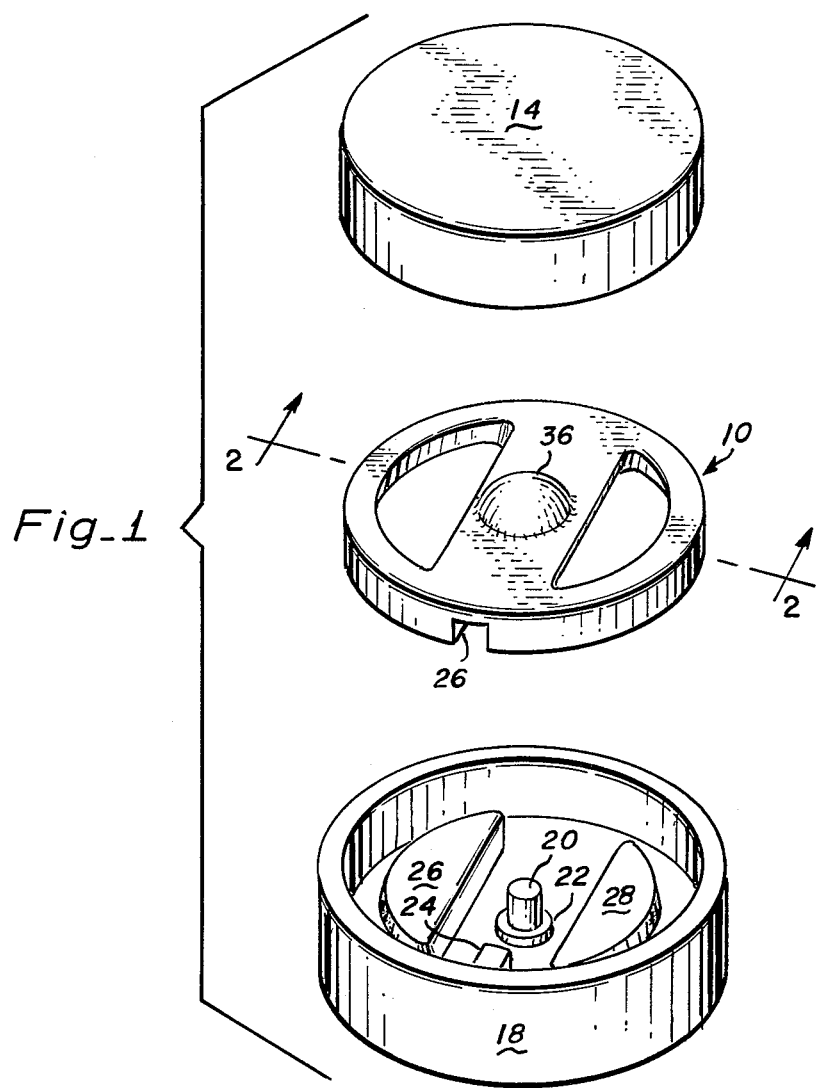
Fig_1
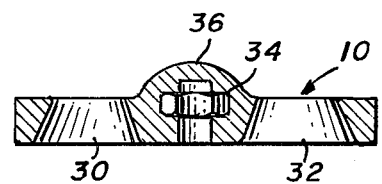
Fig_2

METHOD FOR MAKING MOUNTING RING FOR DENTAL ARTICULATOR

BACKGROUND OF THE INVENTION

This invention relates to dental laboratory equipment and particularly to a novel and improved mounting ring for securing plaster models of dental arches to a dental articulator.

A dental articulator is a well-known dental laboratory tool for adjustably supporting dental casts in a position corresponding to the actual position of the jaws for which dentures are to be made, and includes adjustment provisions by which upper and lower jaws may be moved relative to each other as necessary to accurately depict the occlusal planes of the patient's original teeth. Generally, an articulator includes a stationary base plate for mounting a plaster cast that supports the patient's lower dental arch, and an adjustable and calibrated overlying bow member to which is mounted a plaster cast supporting the upper dental arch.

The arch-supporting plaster casts must be rigidly attached to the base or bow member of the articulator in order to prevent the construction of an improperly formed denture. The plaster casts are, therefore, molded with an internal mounting ring containing a threaded female member adapted to engage the threads of attachment screws extending through the base or bow members of the articulator. In addition, a keyway in the mounting ring is adapted to engage an alignment pin in the base or bow members to prevent possible rotation of the plaster cast around the axis of the screws. Thus, the plaster casts are assembled by pouring the plaster in its liquid state into a mold formed around the mounting ring.

Mounting rings for all types of articulators are readily available in either metal or plastic, both of which provide a good mechanical bond to the attached plaster cast. At the current price range, the typical cost of a ring is between one-half to two dollars per mounting ring. The mounting ring of the present invention may be very rapidly made by the dental laboratory technician at a current material cost of approximately 5 cents per mounting ring and provides not only an effective mechanical bond to an attached arch-supporting plaster cast, but also provides a molecular bond to the cast, thereby resulting in a solid unitary module.

Briefly described, the mounting ring of the invention is constructed of a strong dental stone or other suitable dental plaster which, in its liquid state, is poured into a resilient mold having a cylindrical wall section and a floor section that contains islands for producing the desired internal shape of the mounting ring. A vertical post located on the floor of the mold supports a threaded nut which becomes cast within the plaster mounting ring to be used to attach the mounting ring to the base or bow members of an articulator. After the nut has been placed on the post and the liquid plaster poured, a piston is forced down by hand pressure into the mold to a point where it is stopped by the top surface of the islands, thus removing air pockets in the casting and forcing out the surplus liquid plaster between the sides of the piston and the resilient wall of the mold. When the plaster has hardened, the resiliency of the mold permits easy removal of the completed mounting ring.

In the drawings that illustrate a preferred embodiment of the invention:

FIG. 1 is a perspective view illustrating a mold, piston, and resulting mounting ring; and FIG. 2 is a cross-sectional elevation view of the mounting ring taken along the lines 2—2 of FIG. 1.

DETAILED DESCRIPTION OF THE PREFERRED EMBODIMENT

FIG. 1 is a perspective view illustrating a mounting ring 10 made in accordance with the invention by the use of a resilient mold 12 and a mating piston 14. The resilient mold 12 is formed of a soft resilient material, such as a soft rubber, that may be readily deformed to remove the ring 10. The piston 14 may be made of any suitable material that will not adhere to the ring material and may, if desired, be made of the same resilient material of the mold 12. The mold 12 includes a flat circular floor section 16 and a cylindrical side wall 18. Typically, the thickness of both the floor 16 and side wall 18 is approximately one-quarter inch and the inside diameter of the mold is approximately 2¼ inches.

Centrally located on the floor 16 of the resilient mold 12 is a vertical post 20. Post 20 is provided to support a threaded nut for attachment of the mounting ring 10 to the dental articulator. The diameter of the post must therefore be approximately equal to the root diameter of the threads in the nut so that the nut may slide on the post 20 to rest on the collar 22 which supports the nut above the floor 16 of the mold 12. Typically, the collar 22 is approximately one-eighth inch in width to hold the nut one-eighth inch above the floor 16 and the height of the vertical post is approximately three-eighths of an inch above the floor 16.

In general, all dental articulators have an alignment pin located adjacent the mounting ring attachment screw in order to prevent accidental rotation of the plaster casts around the axis of the screw, and all mounting rings must therefore include a slot or a hole appropriately located to engage the alignment pin. Therefore, the floor 16 of mold 12 includes a radial bar 24 which will form the alignment pin slot 26 in the completed mounting ring 10. The dimensions of the bar 24 will depend upon the dimensions of the alignment pin in the dental articulator and in the preferred embodiment, the bar 24 is typically one-eighth inch wide and one-eighth inch high to produce a corresponding slot 26 in the mounting ring 10.

Also mounted to the floor section 16 of the mold 12 is a pair of tapered islands 26 and 28 which may be any desired shape but which have a flat top surface and a thickness corresponding to the desired thickness of the cast mounting ring 10 to form a stop when piston 14 is forced into the mold 12. In the embodiment illustrated, islands 26 and 28 are chord sections tapered from a small section on the top surface to a larger cross-section at the floor 16 in order to obtain tapered leg sections 30 and 32 that will provide mechanical bonding to a plaster cast.

FIG. 2 is a cross-sectional elevation view of the mounting ring 10 taken along the lines 2—2 of FIG. 1 showing the tapered sections 30 and 32 which provide mechanical bonding to the plaster cast that will eventually be cast over and around the ring 10. Also illustrated in FIG. 2 is a metal nut 34 which is cast into the ring 10. The portion of the ring 10 above nut 34 is preferably provided with a plaster dome 36, as shown, to prevent loss of the nut 34 prior to the application of the plaster cast.

To construct the mounting ring 10, a suitable nut 34 is first placed over the vertical post 20 to rest upon collar 22. Then, dental stone or plaster in liquid form is poured into the resilient mold 12 to a level above the top surfaces of islands 26 and 28. The piston 14, which has a diameter substantially equal to the inside diameter of the mold 12, is then pressed downward into the mold 12 to the point where it is stopped by the top surfaces of islands 26 and 28. The underside of the piston 14 is flat except for a centrally located dome-shaped aperture which forms the protective dome 36 above nut 34. While piston 14 is being pressed into the mold 12, all surplus liquid plaster is easily and readily extruded through the crack between the resilient side wall 18 of mold 12 and the circular surface of the piston 14 and when the dental stone or plaster has sufficiently hardened, the piston 14 is removed and the mounting ring 10, with the nut 34 embedded therein, is easily removed from the soft resilient mold 12 to be used for mounting plaster casts to dental articulators.

It will be noted that the plaster cast that will be used with the mounting ring 10 is of a similar plaster material as that in the mounting ring 10. Therefore, upon application of the liquid of the plaster cast to the mounting ring, there will be a molecular bond between the two plaster bodies in addition to the mechanical bond provided by the tapered leg sections 30 and 32 of FIG. 2. This results in a solid unitary structure with all component materials having substantially the same properties, thus eliminating the possibility of thermal expansion or contraction of various sections with the resulting stresses and possible damage.

Having thus described my invention, what I claim is:

1. The method for producing a mounting ring having a threaded insert for securing dental arch-supporting plaster casts to a dental articulator, said method comprising the steps of:
   providing a resilient mold having substantially cylindrical side walls and a floor portion having a vertical post for supporting a threaded nut, and at least one island having a substantially flat top surface at a distance above said floor corresponding to the desired thickness of said mounting ring;
   providing a piston having a substantially circular cross-section corresponding to the inside diameter of the cylindrical side wall of said resilient mold;
   placing a threaded nut on said vertical post;
   pouring dental plaster in liquid form into said resilient mold to a level that covers the top surface of said island;
   forcing said piston into said resilient mold to the position where it is stopped by the top surface of said island; and
   removing said piston and said mounting ring from said mold.

2. The method claimed in claim 1 wherein said threaded nut is supported on said vertical post at a predetermined spacing above the floor of said mold.

3. The method claimed in claim 2 wherein said piston is formed with a depression on its face for forming a protective dome on the surface of said mounting ring above said threaded nut.

4. The method claimed in claim 3 wherein said resilient mold is formed of soft rubber.

5. The method of claimed in claim 4 wherein said piston is formed of a non-adhering resilient material.

* * * * *